US012594045B2

(12) United States Patent (10) Patent No.: US 12,594,045 B2
Konno et al. (45) Date of Patent: Apr. 7, 2026

(54) CALIBRATION JIG, MAMMOGRAPHY APPARATUS, AND PROGRAM

(71) Applicant: FUJIFILM Corporation, Tokyo (JP)

(72) Inventors: Shinichiro Konno, Kanagawa (JP);
Takashi Tajima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 254 days.

(21) Appl. No.: 18/604,625

(22) Filed: Mar. 14, 2024

(65) Prior Publication Data

US 2024/0324978 A1 Oct. 3, 2024

(30) Foreign Application Priority Data

Mar. 30, 2023 (JP) ................................. 2023-056455

(51) Int. Cl.
*A61B 6/50* (2024.01)
*A61B 6/12* (2006.01)
*A61B 10/02* (2006.01)
*A61B 34/20* (2016.01)

(52) U.S. Cl.
CPC ................ *A61B 6/502* (2013.01); *A61B 6/12* (2013.01); *A61B 10/0233* (2013.01); *A61B 34/20* (2016.02); *A61B 2034/2046* (2016.02)

(58) Field of Classification Search
CPC ............ A61B 34/20; A61B 2034/2051; A61B 2034/2055; A61B 2034/2072; A61B 2090/3983; A61B 10/0233; A61B 90/11; A61B 2034/107; A61B 90/39; A61B 90/37; A61B 2090/365; A61B 5/064; A61B 2090/3937; A61B 2090/0811; A61B 2010/0208; A61B 2090/3941; A61B 2090/3945; A61B 2090/3966; A61B 34/70; A61B 17/17; A61B 2017/00725; A61B 2034/301; A61B 5/061; A61B 17/3403; A61B 2090/3929; A61B 2034/2068; A61B 2090/3908; A61B 90/17
See application file for complete search history.

(56) References Cited

U.S. PATENT DOCUMENTS 5,964,715 A 10/1999 Thunberg

FOREIGN PATENT DOCUMENTS

JP H10-201749 A 8/1998
JP 2010075316 A * 4/2010

* cited by examiner

*Primary Examiner* — Don K Wong
(74) *Attorney, Agent, or Firm* — Studebaker Brackett PLLC

(57) ABSTRACT

A calibration jig is attached to a biopsy apparatus used in combination with a mammography apparatus, and that is for performing calibration to match three-dimensional coordinate systems of the mammography apparatus and the biopsy apparatus, and the calibration jig includes a pseudo biopsy needle that is a pseudo needle of a biopsy needle that is actually used in the biopsy apparatus; and a marker that has a plurality of parts each of which a positional relationship with a needle tip of the pseudo biopsy needle is known.

17 Claims, 11 Drawing Sheets

ERROR INFORMATION DATABASE

| APPLICATION | JIG ID | ERROR INFORMATION | | | | | | |
|---|---|---|---|---|---|---|---|---|
| | | MARKER A | | | MARKER B | | | · · · |
| | | X | Y | Z | X | Y | Z | · · · |
| FOR VERTICAL PUNCTURE | JV001 | +3 | −2 | +4 | −3 | −2 | −2 | · · · |
| | JV002 | −2 | −3 | +2 | +3 | +4 | +2 | · · · |
| | ⋮ | ⋮ | ⋮ | ⋮ | ⋮ | ⋮ | ⋮ | ⋮ |
| FOR LATERAL PUNCTURE | JL001 | +4 | +2 | −2 | +2 | +1 | −2 | · · · |
| | ⋮ | ⋮ | ⋮ | ⋮ | ⋮ | ⋮ | ⋮ | ⋮ |

FIG. 12

CALIBRATION INFORMATION DATABASE

| APPLICATION | JIG ID | CALIBRATION INFORMATION | | |
|---|---|---|---|---|
| | | X | Y | Z |
| FOR VERTICAL PUNCTURE | JVOO1 | −12 | +7 | −8 |
| | JVOO2 | +16 | −8 | +9 |
| | ⋮ | ⋮ | ⋮ | ⋮ |
| FOR LATERAL PUNCTURE | JLOO1 | +7 | +9 | −12 |
| | ⋮ | ⋮ | ⋮ | ⋮ |

FIG. 13

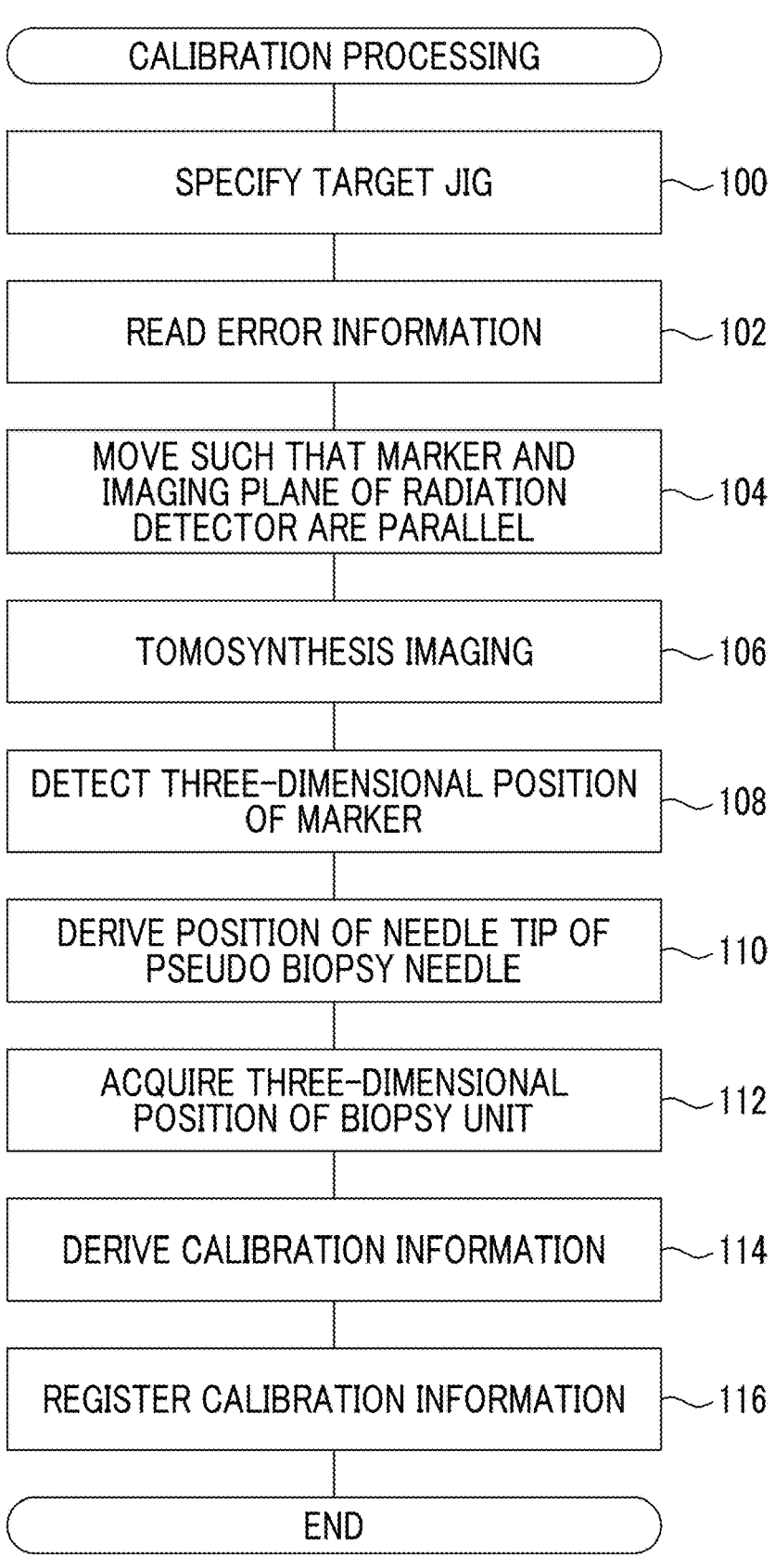

CALIBRATION PROCESSING

SPECIFY TARGET JIG ~100

READ ERROR INFORMATION ~102

MOVE SUCH THAT MARKER AND IMAGING PLANE OF RADIATION DETECTOR ARE PARALLEL ~104

TOMOSYNTHESIS IMAGING ~106

DETECT THREE-DIMENSIONAL POSITION OF MARKER ~108

DERIVE POSITION OF NEEDLE TIP OF PSEUDO BIOPSY NEEDLE ~110

ACQUIRE THREE-DIMENSIONAL POSITION OF BIOPSY UNIT ~112

DERIVE CALIBRATION INFORMATION ~114

REGISTER CALIBRATION INFORMATION ~116

END

RADIATION IMAGE
(FOR VERTICAL PUNCTURE)

RADIATION IMAGE
(FOR LATERAL PUNCTURE)

CALIBRATION JIG, MAMMOGRAPHY APPARATUS, AND PROGRAM

CROSS REFERENCE TO RELATED APPLICATIONS

This application claims priority from Japanese Application No. 2023-056455, filed on Mar. 30, 2023, the entire disclosure of which is incorporated herein by reference.

BACKGROUND

1. Technical Field

The present disclosure relates to a calibration jig, a mammography apparatus, and a non-transitory storage medium storing a program.

2. Related Art

JP1998-201749A (JP-H10-201749A) discloses a method for changing at least one calculation algorithm in a biopsy system that aims to perform improvement in easily specifying positions of specimen samples in a stereotactic biopsy system with high accuracy.

The method is a method for defining at least one calculation algorithm in the biopsy system. In the method for changing at least one calculation algorithm in the biopsy system in which the calculation algorithm influences the decision of the positions of cells or tissue sample regions in a stereotactic biopsy, a phantom in which a specific number of radiopaque markers consisting of rigid radiolucent materials are arranged at known predetermined positions is arranged at a specific position on a target table.

In this method, the phantom is irradiated from two angles to form two images, and the calculation algorithm is changed on the basis of image information and information based on the known position of the marker.

In the related art, in a case where abnormal findings are found in image diagnosis using a mammography apparatus and, as a result of further detailed examination, there are findings that require differentiation between benignancy or malignancy, cells or tissues of a lesion part are collected to obtain a pathological diagnosis result. There is a biopsy apparatus which emits radiation from two or more positions at different angles, specifies a three-dimensional position of the lesion part using two or more radiation images obtained in this manner, and moves a biopsy needle on the basis of the position in a case of collecting the cells or tissues of the lesion part in this case.

The biopsy apparatus recognizes a position of a lesion and a puncture position of the biopsy needle using a three-dimensional coordinate system, and performs movement control of the biopsy needle. Therefore, the position of the lesion and the puncture position of the biopsy needle have to match with high accuracy, but the required accuracy is extremely high (for example, accuracy within +1 mm). For this reason, before using the biopsy apparatus, a coordinate system of the position of the lesion and a coordinate system of the puncture position of the biopsy needle are calibrated, and calibration data for associating these coordinate systems with each other is acquired.

In particular, in a type of an apparatus that is normally used as a mammography apparatus and that is used with a biopsy apparatus attached only in a case of necessary, there is a high possibility that a deviation occurs between the coordinate system of the position of the lesion stored in main body of the mammography apparatus and the coordinate system of the puncture position of the biopsy needle stored in the biopsy apparatus. For this reason, in this type of an apparatus, it is necessary to perform calibration each time the biopsy apparatus is attached.

The calibration at this time can be performed using a phantom of a specific shape provided with a plurality of markers. First, by fixing the phantom with a compression plate and manually aligning the biopsy needle with the position of the marker, position coordinates of the marker indicated by the coordinate system of the biopsy apparatus are acquired. Subsequently, the biopsy needle is moved to a position that does not interfere with imaging, and the phantom is imaged at two or more positions to acquire the position coordinates of the marker indicated by the coordinate system of the mammography apparatus. In a case where there is a deviation between both the acquired position coordinates, the coordinate system of the biopsy apparatus is calibrated so that both the position coordinates match.

In order to minimize the manual work during the calibration described above, a pseudo biopsy needle and a radiopaque marker are attached to the biopsy apparatus, radiography is performed at two or more positions to acquire radiation images, and thereby three-dimensional position coordinates of the mammography apparatus and three-dimensional position coordinates of the biopsy apparatus can be calibrated simultaneously.

However, at this time, in a case where the pseudo biopsy needle and the marker are separate bodies, it is difficult to strictly associate the position of a needle tip of the pseudo biopsy needle with the position of the marker. As a result, there is a problem in that it is not always possible to perform calibration to match the three-dimensional coordinate systems of the mammography apparatus and the biopsy apparatus with high accuracy.

SUMMARY

The present disclosure has been made in view of the above circumstances, and an object thereof is to provide a calibration jig, a mammography apparatus, and a non-transitory storage medium storing a program which can perform calibration to match the three-dimensional coordinate systems of the mammography apparatus and the biopsy apparatus with higher accuracy as compared with a case where the marker and the pseudo biopsy needle are separate bodies.

In order to achieve the object, a calibration jig according to a first aspect of the present disclosure is a calibration jig attached to a biopsy apparatus used in combination with a mammography apparatus, and that is for performing calibration to match three-dimensional coordinate systems of the mammography apparatus and the biopsy apparatus, and the calibration jig includes a pseudo biopsy needle that is a pseudo needle of a biopsy needle that is actually used in the biopsy apparatus; and a marker that has a plurality of parts each of which a positional relationship with a needle tip of the pseudo biopsy needle is known.

In a calibration jig according to a second aspect of the present disclosure, in the calibration jig according to the first aspect, the marker may be a plurality of markers each having any one of the plurality of parts individually.

In a calibration jig according to a third aspect of the present disclosure, in the calibration jig according to the first aspect, a position of the needle tip of the pseudo biopsy needle is different from a position of the marker.

In a calibration jig according to a fourth aspect of the present disclosure, in the calibration jig according to the first aspect, the marker may have a spherical shape or a flat plate shape.

In the calibration jig according to the first aspect, a calibration jig according to a fifth aspect of the present disclosure may further include an opening portion which allows the needle tip of the pseudo biopsy needle to be accessed from an external jig.

In a calibration jig according to a sixth aspect of the present disclosure, in the calibration jig according to the fifth aspect, the opening portion may allow the access from at least two directions.

In a calibration jig according to a seventh aspect of the present disclosure, in the calibration jig according to the sixth aspect, the direction of the access may be a direction different from an axial direction of a straight line connecting the needle tip of the pseudo biopsy needle and the plurality of parts of the marker.

In a calibration jig according to an eighth aspect of the present disclosure, in the calibration jig according to the first aspect, the plurality of parts may be positioned on a surface parallel to a radiation detection surface of the mammography apparatus.

In order to achieve the object, a mammography apparatus according to a ninth aspect of the present disclosure is a mammography apparatus provided with a biopsy apparatus having the calibration jig of the present disclosure, a radiation irradiator, and a radiation detector that captures a radiation image using radiation emitted from the radiation irradiator, the mammography apparatus including at least one processor, wherein the processor detects three-dimensional position coordinates of the plurality of parts in the marker of the calibration jig, derives three-dimensional position coordinates of the needle tip of the pseudo biopsy needle using the detected three-dimensional position coordinates of the plurality of parts, and performs calibration to match the derived three-dimensional position coordinates of the needle tip and the three-dimensional position coordinates of the needle tip of the pseudo biopsy needle of the biopsy apparatus.

In a mammography apparatus according to a tenth aspect of the present disclosure, in the mammography apparatus according to the ninth aspect, the processor may correct a manufacturing deviation of a positional relationship between the pseudo biopsy needle and the plurality of parts.

In a mammography apparatus according to an eleventh aspect of the present disclosure, in the mammography apparatus according to the ninth aspect, the processor may arrange the marker of the calibration jig in parallel with the radiation detector in a case of detecting the three-dimensional position coordinates of the plurality of parts.

In a mammography apparatus according to a twelfth aspect of the present disclosure, in the mammography apparatus according to the ninth aspect, the calibration jig may be moved in a three-dimensional space by the biopsy apparatus.

In a mammography apparatus according to a thirteenth aspect of the present disclosure, in the mammography apparatus according to the ninth aspect, the calibration jig may be for at least one of vertical puncture or lateral puncture.

In a mammography apparatus according to a fourteenth aspect of the present disclosure, in the mammography apparatus according to the ninth aspect, the processor may detect the three-dimensional position coordinates of the plurality of parts using a plurality of radiation images obtained by the radiation detector in a state where irradiation directions of the radiation from the radiation irradiator are different.

In a mammography apparatus according to a fifteenth aspect of the present disclosure, in the mammography apparatus according to the fourteenth aspect, the processor may detect the three-dimensional position coordinates of the plurality of parts at a plurality of positions by moving the calibration jig in a three-dimensional space, and derive the three-dimensional position coordinates of the needle tip at the plurality of positions using the detected three-dimensional position coordinates of the plurality of parts.

In a mammography apparatus according to a sixteenth aspect of the present disclosure, in the mammography apparatus according to the fifteenth aspect, the processor may perform the calibration using the derived three-dimensional position coordinates of the needle tip at the plurality of positions.

In order to achieve the object, a non-transitory storage medium storing a program according to a seventeenth aspect of the present disclosure is a program executed in a mammography apparatus provided with a biopsy apparatus having the calibration jig of the present disclosure, a radiation irradiator, and a radiation detector that captures a radiation image using radiation emitted from the radiation irradiator, the program causing a computer to execute detecting three-dimensional position coordinates of the plurality of parts in the marker of the calibration jig, deriving three-dimensional position coordinates of the needle tip of the pseudo biopsy needle using the detected three-dimensional position coordinates of the plurality of parts, and performing calibration to match the derived three-dimensional position coordinates of the needle tip and the three-dimensional position coordinates of the needle tip of the pseudo biopsy needle of the biopsy apparatus.

According to the present disclosure, it is possible to perform calibration to match the three-dimensional coordinate systems of the mammography apparatus and the biopsy apparatus with higher accuracy as compared with a case where the marker and the pseudo biopsy needle are separate bodies.

5

Figure 9:
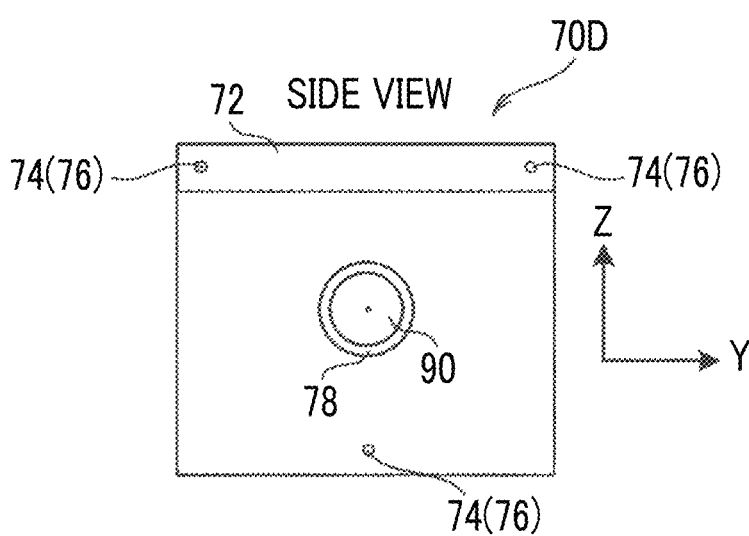

FIG. 9 is a schematic configuration diagram illustrating another example of the calibration jig (for lateral puncture) according to the embodiment.

Figures 10, 11:
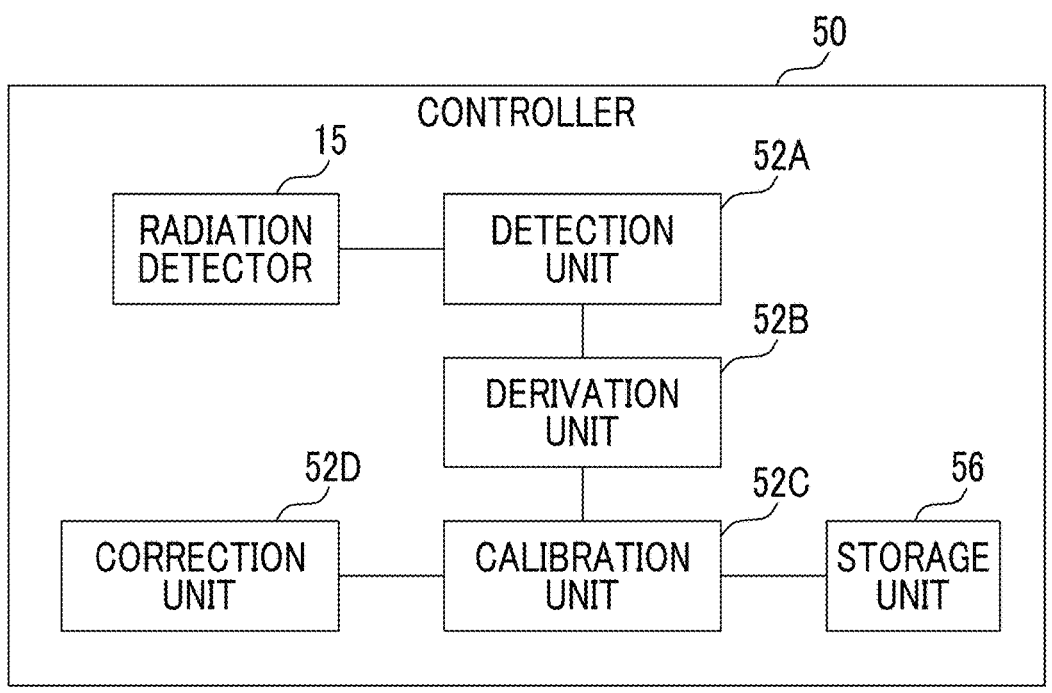

FIG. 10 is a functional block diagram illustrating a functional configuration of a controller provided in the mammography apparatus according to the embodiment.

FIG. 11 is a schematic diagram illustrating an example of a configuration of an error information database according to the embodiment.

FIG. 12 is a schematic diagram illustrating an example of a configuration of a calibration information database according to the embodiment.

FIG. 13 is a flowchart illustrating an example of calibration processing according to the embodiment.

Figure 14:
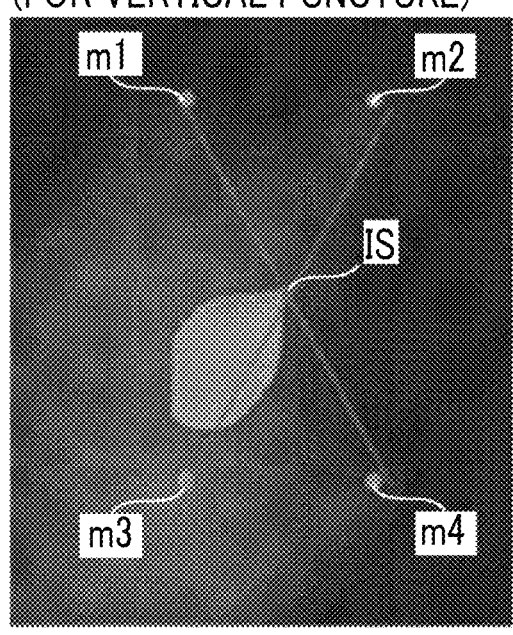

FIG. 14 is a diagram illustrating an example of a radiation image in a case where a calibration jig for the vertical puncture is used as the calibration jig, which is obtained in the calibration processing according to the embodiment.

Figure 15:
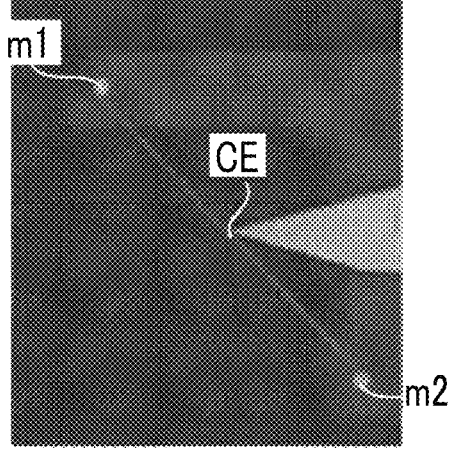

FIG. 15 is a diagram illustrating an example of a radiation image in a case where a calibration jig for the lateral puncture is used as the calibration jig, which is obtained in the calibration processing according to the embodiment.

Figure 16:
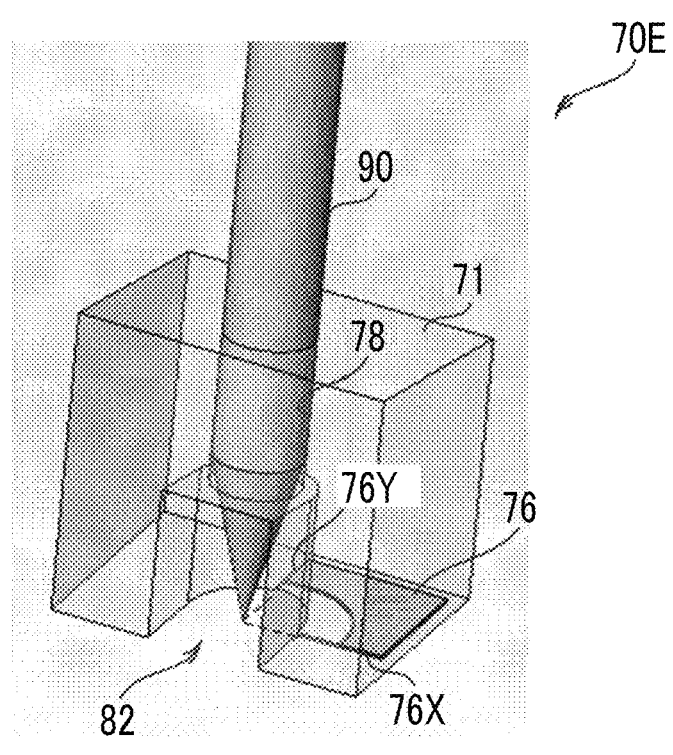

FIG. 16 is a schematic configuration diagram illustrating another example of the calibration jig (for vertical puncture) according to the embodiment.

DESCRIPTION EMBODIMENTS

Figure 1:
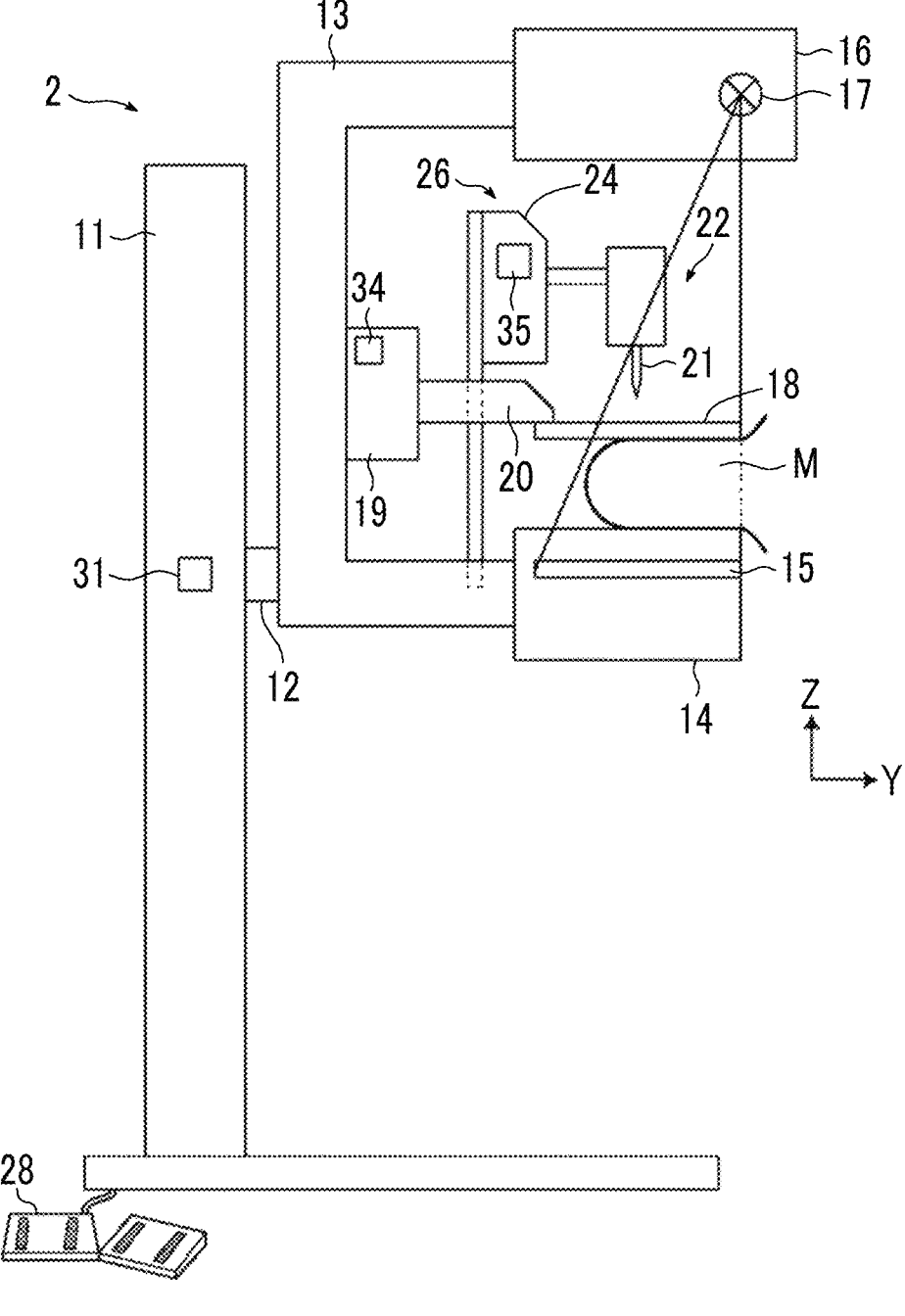
FIG. 1 is a schematic configuration diagram illustrating an example of a mammography apparatus according to an embodiment.

Hereinafter, embodiments for implementing the technique of the present disclosure will be described in detail with reference to the drawings. First, a mammography apparatus 2 of the present embodiment will be described in detail using FIGS. 1 to 4. FIG. 1 is a schematic configuration diagram illustrating an example of the mammography apparatus 2 according to the present embodiment.

As an example, as illustrated in FIG. 1, in the mammography apparatus 2 according to the present embodiment, a radiation housing portion 16 that houses a radiation irradiator 17 therein and an imaging table 14 are connected to an arm 13 to face each other. An image recording medium such as a radiation detector 15 is set inside the imaging table 14 in a state of being accommodated in a recording medium holding portion such as a cassette. The arm 13 is attached to a base 11 with a C axis 12. In addition, the arm 13 is provided to the base 11 by attaching the C axis 12, which is the center of rotation, to a center position of the radiation detector 15 such that the center of rotation of the arm 13 is the center of the radiation detector 15 in an X direction (refer to FIG. 2).

The base 11 is provided with an operation unit 28 that accepts an irradiation instruction for radiation from the radiation irradiator 17 and is for an operator to adjust the height of the imaging table 14 (that is, the height of the arm 13) and the inclination of the imaging table 14 (that is, the inclination of the arm 13), and with an arm controller 31 that moves the arm 13 vertically and rotationally according to an input from the operation unit 28.

The arm controller 31 adjusts the inclination of the arm 13 by rotating the C axis 12 attached to the base 11, and adjusts the height of the imaging table 14 by vertically moving the arm 13.

At a central portion of the arm 13, a compression plate 18 that is disposed above the imaging table 14 to hold and compress the breast, a support portion 20 that supports the compression plate 18, and a moving mechanism 19 that moves the support portion 20 in an up and down direction along the arm 13. The position and compression pressure of the compression plate 18 are controlled by a compression plate controller 34.

Figure 2:
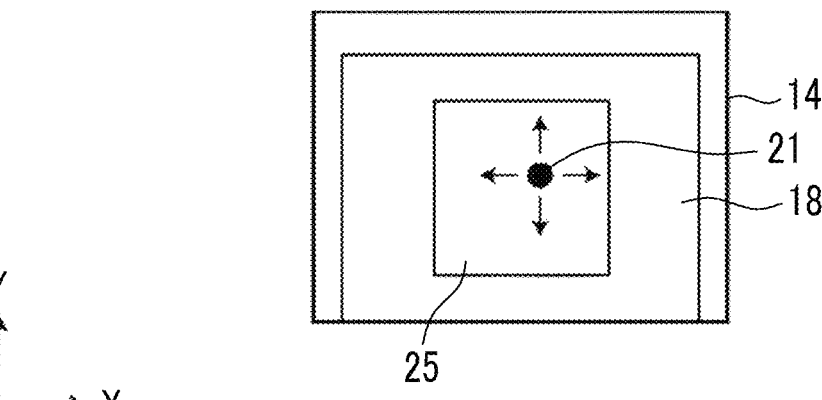
FIG. 2 is a schematic plan view of a compression plate in the mammography apparatus according to the embodiment, viewed from above.

FIG. 2 is a view of the compression plate 18 viewed from above. As illustrated in FIG. 2, the compression plate 18 is provided with an opening portion 25 of approximately 10×10 cm square such that a biopsy can be performed with the breast fixed by the imaging table 14 and the compression plate 18.

As an example, a biopsy unit 26 as the biopsy apparatus of the present disclosure illustrated in FIG. 1 includes a biopsy needle 21 that punctures the breast, and a biopsy needle unit 22, and further includes a moving mechanism 24 that moves the biopsy needle unit 22 in X, Y, and Z directions. The position of a distal end of the biopsy needle 21 of the biopsy needle unit 22 is controlled by a needle position controller 35 of the moving mechanism 24. Note that in FIG. 2, a horizontal direction is the X direction, a vertical direction is the Y direction, and a direction perpendicular to an XY plane is the Z direction.

Figure 3:
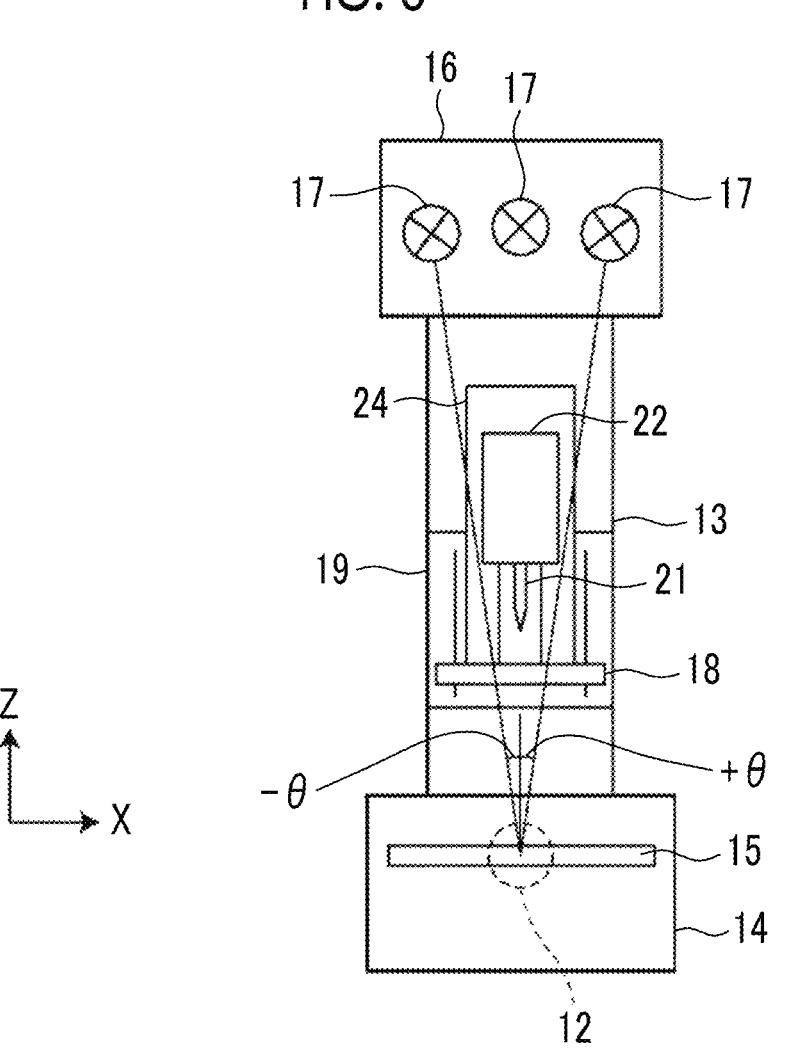
FIG. 3 is a diagram illustrating an example of a state in a case where a radiation irradiator in the mammography apparatus according to the embodiment is tilted left and right from a direction along an arm.

Note that, in the mammography apparatus 2, scout images captured from two directions so as to include a target region of the breast to be biopsied are acquired before performing puncture. The scout image is an image viewed from different viewpoints in order to check the position to be pathologically examined. For example, as illustrated in FIG. 3, two partial images obtained by performing imaging from directions in which the radiation irradiator 17 is tilted left and right (for example, tilted by 15° in the directions of +θ and −θ illustrated in FIG. 3) from a direction along the arm 13 are set as the scout images.

Figure 4:
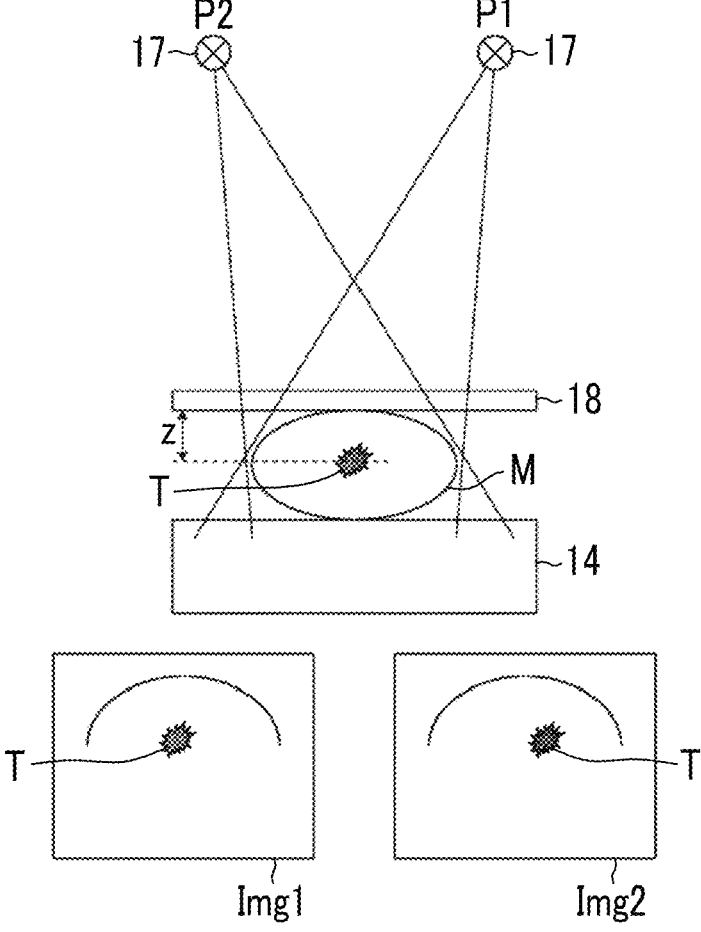
FIG. 4 is a diagram illustrating an example of a relationship between the positions of the radiation irradiator in the mammography apparatus according to the embodiment and two scout images.

FIG. 4 is a diagram illustrating an example of a relationship between the positions of the radiation irradiator 17 and two scout images. In a scout image Img1 obtained by performing imaging with the radiation irradiator 17 placed at a position P1, the position of a target T appears to be close to the left side, and in a scout image Img2 obtained by performing imaging with the radiation irradiator 17 placed at a position P2, the position of the target T appears to be close to the right side. From the deviation of the target T between the two scout images Img1 and Img2, a distance z from a bottom surface of the compression plate 18 (the side that presses the breast) to the target T and the position on the XY plane are obtained, and thereby three-dimensional positional information of the target T can be obtained.

In a case where the needle position controller 35 of the biopsy unit 26 receives the positional information of the target T, the needle position controller 35 moves the position of the distal end of the biopsy needle 21 to the position of the target T, and performs the puncture on the breast with the biopsy needle 21.

Figure 5:
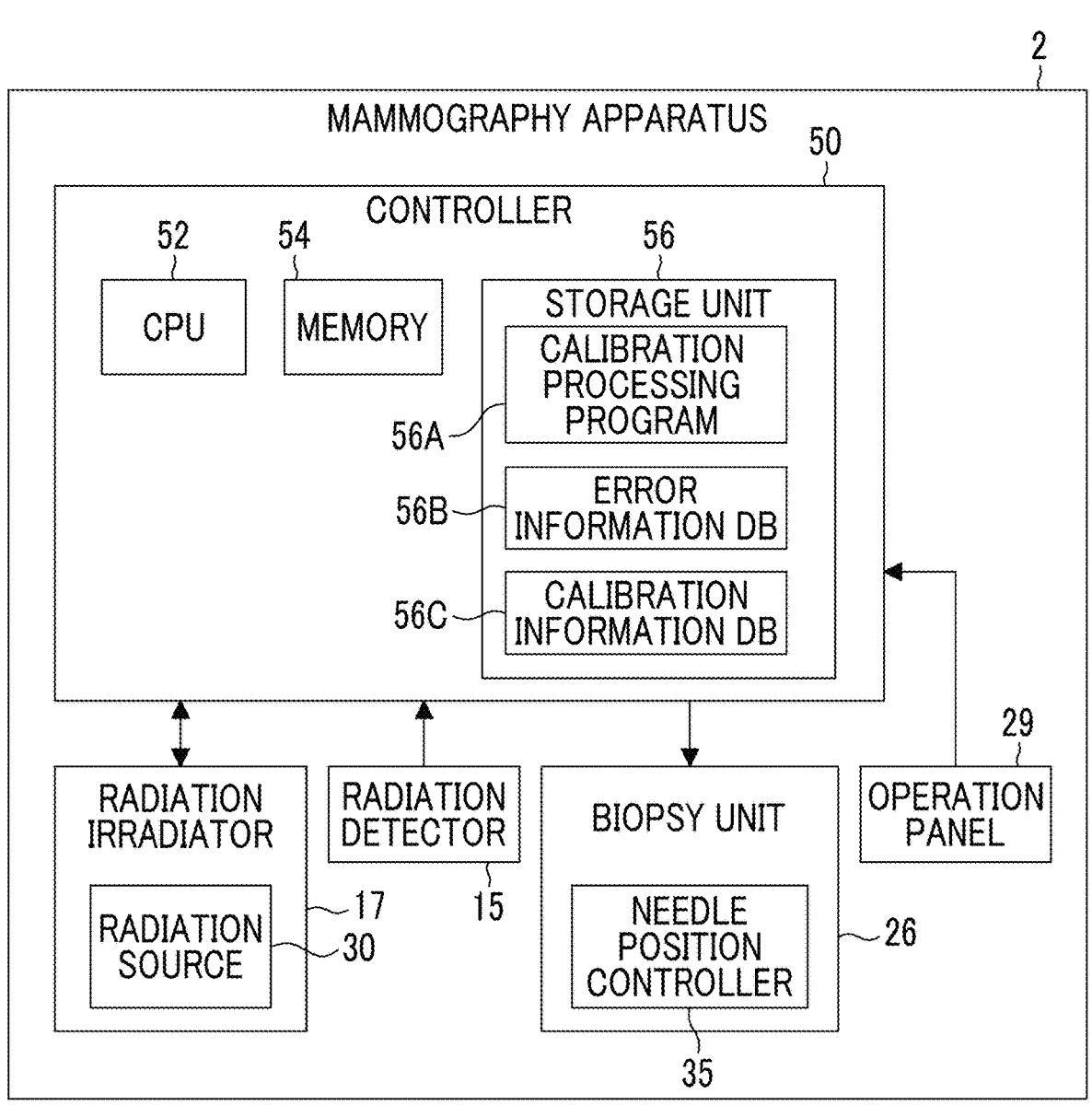
FIG. 5 is a block diagram illustrating an example of an electrical configuration of the mammography apparatus according to the embodiment.

Next, an electrical configuration of the mammography apparatus 2 according to the present embodiment will be described with reference to FIG. 5. FIG. 5 is a block diagram illustrating an example of the electrical configuration of the mammography apparatus according to the present embodiment.

The mammography apparatus 2 according to the present embodiment includes an operation panel 29 and a controller 50 in addition to the radiation detector 15, the radiation irradiator 17, and the biopsy unit 26 described above.

The controller 50 has functions to control the entire operation of the mammography apparatus 2, and includes a central processing unit (CPU) 52 as a processor, a memory 54 including a read only memory (ROM) and a random access memory (RAM), and a nonvolatile storage unit 56 including a hard disk drive (HDD), a flash memory, and the like. In addition, the controller 50 is connected to the radiation irradiator 17, the radiation detector 15, the biopsy unit 26, and the operation panel 29.

In a case where the controller 50 receives an irradiation instruction from the operator via the operation panel 29 (exposure switch), the controller 50 causes a radiation source 30 provided in the radiation irradiator 17 to irradiate an upper surface of the imaging table 14 with radiation according to an imaging menu set on the basis of designated exposure conditions.

The radiation detector 15 records image information by being irradiated with radiation carrying image information, and outputs the recorded image information. For example, the radiation detector 15 is configured as a flat panel detector (FPD) that includes a radiation-sensitive layer and that converts radiation into digital data and outputs the digital data. In a case where the radiation detector 15 is irradiated with radiation, the radiation detector 15 outputs the image information indicating a radiation image to the controller 50. In the present embodiment, the radiation detector 15 receives irradiation of the radiation that has passed through a breast M to obtain image information indicating the radiation image.

The operation panel 29 has a function of setting various kinds of operation information such as exposure conditions and posture information, various operation instructions, and the like.

The exposure conditions set in the operation panel 29 include information such as tube voltage, tube current, irradiation time, and posture information. The posture information designated in the operation panel 29 includes information representing an imaging position (imaging posture, angle) in a case of imaging the breast M from a plurality of directions.

Note that the various kinds of operation information such as exposure conditions and posture information, various operation instructions, and the like may be set by the operator using the operation panel 29, may be obtained from another control device (radiology information system (RIS), a radiation information system, a system that manages information on medical treatment, diagnosis, and the like using radiation) and the like, or may be stored in advance in a storage unit.

In a case where various kinds of information are set from the operation panel 29, the controller 50 causes the radiation irradiator 17 to irradiate an imaging part (breast M) of a subject with radiation according to the imaging menu set on the basis of the various kinds of set information, and captures the radiation image. In a case of performing tomosynthesis imaging in which imaging is performed from a plurality of directions, the controller 50 adjusts the posture of the arm 13 so that the radiation irradiator 17 is positioned above the upper surface of the imaging table 14. Then, in a state substantially similar to that illustrated in FIG. 3, the controller 50 rotates the arm 13 to move the radiation irradiator 17 in an arc shape from a predetermined initial angle by a predetermined step size angle, and causes the radiation source 30 provided in the radiation irradiator 17 to individually irradiate the upper surface of the imaging table 14 with radiation at different angles on the basis of the imaging condition. As a result, a plurality of radiation images can be obtained.

The needle position controller 35 provided in the biopsy unit 26 drives the biopsy unit 26 to move the biopsy needle 21 to a predetermined position and holds the biopsy needle 21 in a state where the biopsy needle 21 is tilted to an insertion angle, in response to the instruction from the controller 50.

In addition, a calibration processing program 56A is stored in the storage unit 56 as a storage medium included in the controller 50 according to the present embodiment. The CPU 52 reads the calibration processing program 56A from the storage unit 56 to expand the calibration processing program 56A in the memory 54, and executes the expanded calibration processing program 56A. In addition, an error information database 56B and a calibration information database 56C are stored in the storage unit 56. Details of these databases will be described later.

Figure 6:
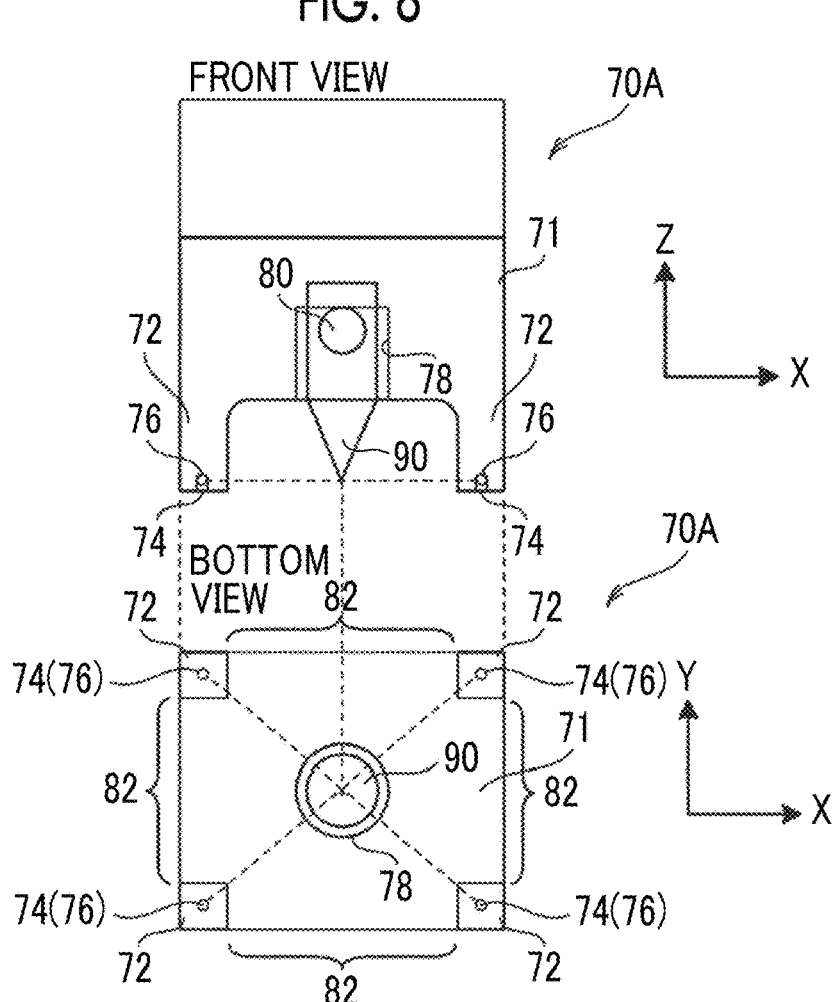
FIG. 6 is a schematic configuration diagram illustrating an example of a calibration jig (for vertical puncture) according to the embodiment.
Figure 7:
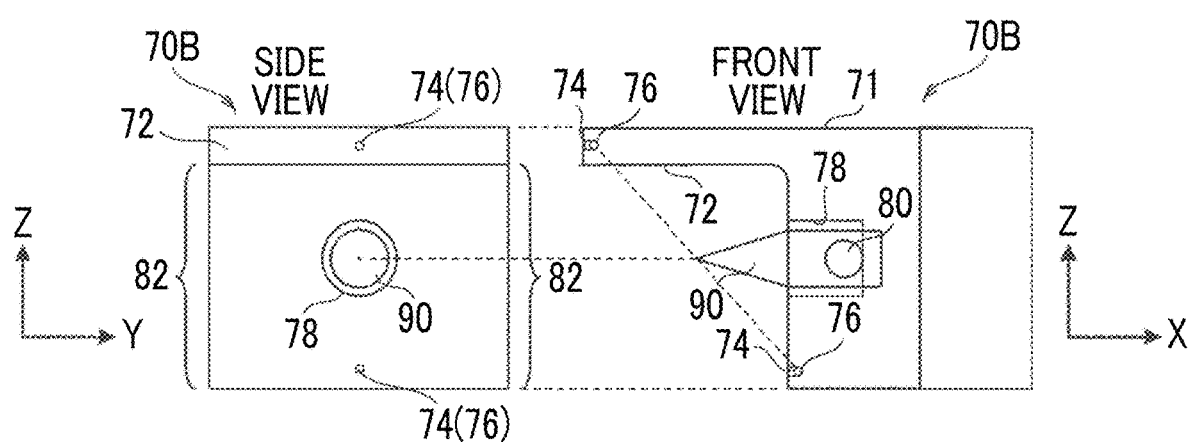
FIG. 7 is a schematic configuration diagram illustrating an example of a calibration jig (for lateral puncture) according to the embodiment.

On the other hand, in the mammography apparatus 2 according to the present embodiment, a calibration jig is prepared which is provided in the biopsy unit 26 instead of being provided in the biopsy needle unit 22 and which is for performing calibration to match the three-dimensional coordinate systems of the mammography apparatus 2 and the biopsy unit 26. Hereinafter, configurations of a calibration jig 70A and a calibration jig 70B according to the present embodiment will be described with reference to FIGS. 6 and 7. FIG. 6 is a schematic configuration diagram illustrating an example of the calibration jig (for vertical puncture) according to the present embodiment. In addition, FIG. 7 is a schematic configuration diagram illustrating an example of the calibration jig (for lateral puncture) according to the present embodiment. Note that, in the following, a case of describing calibration jigs such as the calibration jig 70A and the calibration jig 70B without distinguishing them, the calibration jig is collectively referred to as a "calibration jig 70".

First, the configuration of the calibration jig 70A for vertical puncture will be described with reference to FIG. 6. As an example, as illustrated in FIG. 6, the calibration jig 70A for vertical puncture according to the present embodiment includes a substantially rectangular parallelepiped jig main body 71, and a substantially rectangular parallelepiped protruding portion 72 is provided at each of four corners of a bottom surface of the jig main body 71.

In addition, a depression 74 is provided at the central portion of the bottom surface of each of the four protruding portions 72, and a marker 76 is embedded in each depression 74. The marker 76 according to the present embodiment does not transmit radiation, and has a relatively small spherical shape (in the present embodiment, a sphere with a diameter of 0.5 mm).

On the other hand, a mounting hole 78 to which a pseudo biopsy needle 90 is attached is provided at the central portion on the bottom surface of the jig main body 71. As illustrated in FIG. 6, the pseudo biopsy needle 90 according to the present embodiment has a cylindrical shape of which one end portion is conical, and is fixed to the jig main body 71 by a fastener 80 in a state where the other end portion side is inserted into the mounting hole 78. The pseudo biopsy needle 90 is a pseudo model of the biopsy needle 21, and the distal end portion of the conical portion corresponds to the needle tip of the biopsy needle 21. Therefore, hereinafter, the distal end portion will also be referred to as the needle tip of the pseudo biopsy needle 90.

In the calibration jig 70A according to the present embodiment, the pseudo biopsy needle 90 and the four markers 76 are positioned such that the position of an intersection of two straight lines in a case of connecting a pair of opposing markers 76 with the straight line matches the position of the needle tip of the pseudo biopsy needle 90.

In the mammography apparatus 2 according to the present embodiment, in order to recognize the three-dimensional position coordinates of the needle tip of the pseudo biopsy needle 90 with high accuracy as necessary, a coordinate recognition jig (not illustrated) is provided in which the position of the distal end portion matches the position of the needle tip of the pseudo biopsy needle 90 and the other end portion is fixed to the mammography apparatus 2.

On the other hand, as illustrated in FIG. 6, in the calibration jig 70A according to the present embodiment, since the needle tip of the pseudo biopsy needle 90 is surrounded by the four protruding portions 72, four opening portions 82 are formed which allow the needle tip of the pseudo biopsy needle 90 to be accessed from the coordinate recognition jig described above. That is, in the calibration jig 70A according to the present embodiment, the opening portions 82 are provided in four directions with the pseudo biopsy needle 90 as the center. Therefore, the coordinate recognition jig can access the needle tip of the pseudo biopsy needle 90 from the four directions. In addition, in the calibration jig 70A according to the present embodiment, since the direction of the access is different from an axial direction of the straight line connecting the needle tip of the pseudo biopsy needle 90 and the plurality of parts of the technique of the present disclosure in the markers 76 (center portion of each marker 76 in the present embodiment), the coordinate recognition jig can access the needle tip of the pseudo biopsy needle 90 without any obstacles.

Next, the configuration of the calibration jig 70B for lateral puncture will be described with reference to FIG. 7. Note that, in FIG. 7, parts having similar roles as the calibration jig 70A for vertical puncture illustrated in FIG. 6 are given the same reference numerals as in FIG. 6.

As an example, as illustrated in FIG. 7, the calibration jig 70B for lateral puncture according to the present embodiment includes a substantially rectangular parallelepiped jig main body 71, and a substantially rectangular parallelepiped protruding portion 72 is provided on a side portion on the upper surface side of a side surface of the jig main body 71.

In addition, the depression 74 is provided at the central portion of an end portion of the protruding portion 72 on a side opposite to the jig main body 71, and the marker 76 which does not transmit radiation and has a spherical shape and which is similar to that in the calibration jig 70A is embedded in the depression 74.

In addition, the depression 74 is provided at the central portion in the vicinity of one side portion on the lower surface side of the side surface of the jig main body 71, and the marker 76 similar to that in the calibration jig 70A is embedded in the depression 74.

On the other hand, the mounting hole 78 to which the pseudo biopsy needle 90 is attached is provided at the central portion on the side surface of the jig main body 71 on a side close to the protruding portion 72. As illustrated in FIG. 7, the pseudo biopsy needle 90 according to the present embodiment is fixed to the jig main body 71 by the fastener 80 in a state where an end portion on a side opposite to the needle tip is inserted into the mounting hole 78.

In the calibration jig 70B according to the present embodiment, the pseudo biopsy needle 90 and the two markers 76 are positioned such that the position of the center of the straight line in a case of connecting a pair of markers 76 with the straight line matches the position of the needle tip of the pseudo biopsy needle 90.

As illustrated in FIG. 7, in the calibration jig 70B according to the present embodiment, since the needle tip of the pseudo biopsy needle 90 is positioned closer to the jig main body 71 than the distal end portion of the protruding portion 72, two opening portions 82 are formed which allow the needle tip of the pseudo biopsy needle 90 to be accessed from the coordinate recognition jig described above. Accordingly, in the calibration jig 70B according to the present embodiment, the opening portions 82 are provided in two directions with the pseudo biopsy needle 90 as the center. Therefore, the coordinate recognition jig can access the pseudo biopsy needle 90 from the two directions. In addition, in the calibration jig 70B according to the present embodiment, since the direction of the access is different from an axial direction of the straight line connecting the needle tip of the pseudo biopsy needle 90 and the plurality of parts of the markers 76, the coordinate recognition jig can access the needle tip of the pseudo biopsy needle 90 without any obstacles.

Note that the reason why the marker 76 used in the calibration jig 70 has a spherical shape is as follows. That is, in the mammography apparatus 2 according to the present embodiment, the three-dimensional coordinate position of the marker 76 is detected from the radiation image obtained by tomosynthesis imaging as will be described later. On the other hand, in the tomosynthesis imaging, it is necessary to find a tomogram with the best focal position, and it is advantageous from this point of view to use a marker 76 having a spherical shape.

In this manner, in the present embodiment, for example, the calibration jig 70A for vertical puncture and the calibration jig 70B for lateral puncture respectively illustrated in FIGS. 6 and 7 are used as the calibration jig 70, but the configuration of the calibration jig 70 is not limited to those illustrated in FIGS. 6 and 7.

Figure 8:
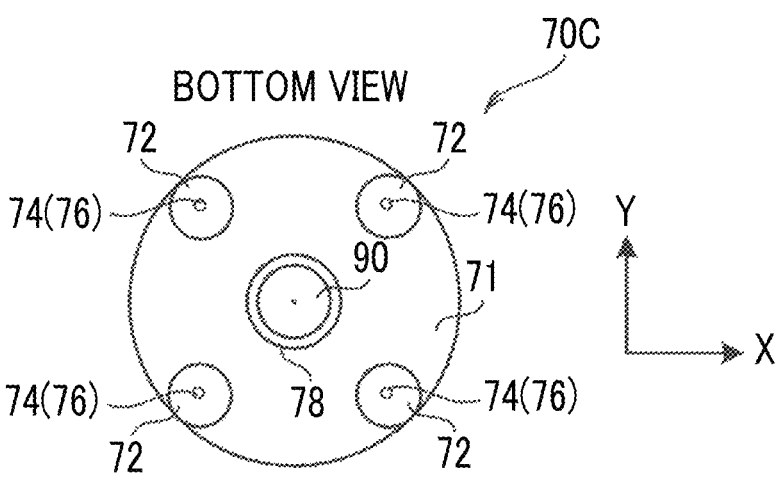
FIG. 8 is a schematic configuration diagram illustrating another example of the calibration jig (for vertical puncture) according to the embodiment.

FIG. 8 illustrates a schematic configuration diagram illustrating another example of a calibration jig 70C for vertical puncture according to the present embodiment. Note that, in FIG. 8, only the bottom view of the calibration jig 70C is illustrated, but illustration of the front view is omitted because the front view is substantially similar to the calibration jig 70A illustrated in FIG. 6.

As illustrated in FIG. 8, this calibration jig 70C has the jig main body 71 having a cylindrical shape, and the protruding portions 72 each having a cylindrical shape are provided at equal intervals in the vicinity of the circumferential portion of the bottom surface of the jig main body 71. Note that, similar to the calibration jig 70A, in the protruding portion 72, the marker 76 that does not transmit radiation and has a spherical shape is embedded in the depression 74.

On the other hand, FIG. 9 illustrates a schematic configuration diagram illustrating another example of a calibration jig 70D for lateral puncture according to the present embodiment. Note that, in FIG. 9, only the side view of the calibration jig 70D is illustrated, but illustration of the front view is omitted because the front view is substantially similar to the calibration jig 70B illustrated in FIG. 7.

As illustrated in FIG. 9, in the calibration jig 70D, the marker 76 which does not transmit radiation and has a spherical shape is embedded in the depression 74 at the end portion of the protruding portion 72 on a side opposite to the jig main body 71 and in the vicinity of both end portions. Accordingly, the calibration jig 70D is provided with three markers 76.

Similarly to the calibration jig 70A and the calibration jig 70B, the calibration jig 70C and the calibration jig 70D are also suitable for the calibration to match the three-dimensional coordinate systems of the mammography apparatus 2 and the biopsy unit 26.

Next, the functional configuration of the controller 50 according to the present embodiment will be described with reference to FIG. 10. FIG. 10 is a functional block diagram illustrating a functional configuration of the controller 50 provided in the mammography apparatus 2 according to the present embodiment.

As illustrated in FIG. 10, the controller 50 includes a detection unit 52A, a derivation unit 52B, a calibration unit 52C, and a correction unit 52D. The CPU 52 executes the calibration processing program 56A to function as the detection unit 52A, the derivation unit 52B, the calibration unit 52C, and the correction unit 52D.

The detection unit 52A according to the present embodiment detects the three-dimensional position coordinates of the plurality of parts in the markers 76 of the calibration jig 70. In addition, the derivation unit 52B according to the present embodiment derives the three-dimensional position coordinates of the needle tip of the pseudo biopsy needle 90 using the three-dimensional position coordinates of the plurality of parts detected by the detection unit 52A. Then, the calibration unit 52C according to the present embodiment performs calibration to match the three-dimensional position coordinates of the needle tip of the pseudo biopsy needle 90 derived by the derivation unit 52B and the three-dimensional position coordinates of the needle tip of the pseudo biopsy needle 90 of the biopsy unit 26. Furthermore, the correction unit 52D according to the present embodiment corrects the manufacturing deviation in the positional relationship between the pseudo biopsy needle 90 and the plurality of parts.

Here, the detection unit 52A according to the present embodiment arranges the marker 76 of the calibration jig 70 in parallel with the radiation detector 15 in a case of detecting the three-dimensional position coordinates of the plurality of parts. In addition, the calibration jig 70 according to the present embodiment is moved in a three-dimensional space by the biopsy unit 26.

In addition, the detection unit 52A according to the present embodiment detects the three-dimensional position coordinates of the plurality of parts using a plurality of radiation images obtained by the radiation detector 15 in a state where the irradiation directions of the radiation from the radiation irradiator 17 are different. Note that, in the present embodiment, the plurality of radiation images are obtained by tomosynthesis imaging, but the present disclosure is not limited thereto. For example, the plurality of radiation images may be obtained by the similar operation as in a case of acquiring the scout image described above.

Next, the error information database 56B according to the present embodiment will be described with reference to FIG. 11. FIG. 11 is a schematic diagram illustrating an example of a configuration of the error information database 56B according to the present embodiment.

The error information database 56B according to the present embodiment is a database in which information is registered, the information being used for the correction unit 52D described above to correct the manufacturing deviation in the positional relationship between the pseudo biopsy needle 90 and the plurality of parts. As illustrated in FIG. 11, the error information database 56B according to the present embodiment stores each piece of information of application, jig identification (ID), and error information.

The application is information indicating the different applications for vertical puncture and lateral puncture, and the jig ID is information assigned in advance to each calibration jig 70 in order to individually identify the calibration jig 70 to which the biopsy unit 26 corresponds. In addition, the error information is information indicating the amount of manufacturing deviation in the positional relationship between the pseudo biopsy needle 90 and the above part in the three-dimensional space for each of the plurality of markers 76 provided in the corresponding calibration jig 70.

In the present embodiment, an examiner of the calibration jig 70 or the like acquires error information by actually measuring the calibration jig 70 using a dedicated measuring instrument after manufacturing the calibration jig 70. Then, the error information database 56B according to the present embodiment is constructed by registering the acquired error information in the storage unit 56 of the controller 50 of the mammography apparatus 2. However, the present disclosure is not limited to this form, and for example, error information may be automatically acquired and registered without human intervention.

Next, the calibration information database 56C according to the present embodiment will be described with reference to FIG. 12. FIG. 12 is a schematic diagram illustrating an example of a configuration of the calibration information database 56C according to the present embodiment.

As illustrated in FIG. 12, the calibration information database 56C according to the present embodiment stores each piece of information of application, jig ID, and calibration information.

The application and the jig ID are the same information as the application and the jig ID of the error information database 56B, respectively. Then, the calibration information is information registered for each corresponding calibration jig 70 by calibration processing (refer to also FIG. 13) described later.

Next, the operation of the mammography apparatus 2 according to the present embodiment will be described with reference to FIG. 13. The CPU 52 in the controller 50 of the mammography apparatus 2 executes the calibration processing program 56A, so that the calibration processing illustrated in FIG. 13 is executed. The calibration processing illustrated in FIG. 13 is executed, for example, in a case where the biopsy unit 26 is attached to the mammography apparatus 2. Note that, in order to avoid complications, a case will be described here in which the error information database 56B has been constructed and one of the calibration jigs 70 has been mounted in the biopsy unit 26.

In Step 100 of FIG. 13, the CPU 52 specifies the calibration jig 70 mounted in the biopsy unit 26. Note that, in the present embodiment, the calibration jig 70 is specified by the needle position controller 35 of the biopsy unit 26 receiving the jig ID assigned to the calibration jig 70 mounted therein, but the form of specifying the calibration jig 70 is not limited thereto. For example, the calibration jig 70 may be specified by the operator of the mammography apparatus 2 inputting the jig ID of the calibration jig 70 mounted in the biopsy unit 26 via the operation panel 29 or the like.

In Step 102, the CPU 52 reads error information corresponding to the jig ID of the specified calibration jig 70 (hereinafter referred to as "target jig") from the error information database 56B. In Step 104, the CPU 52 transmits instruction information to the needle position controller 35 of the biopsy unit 26 to perform control such that the position of the center portion of the plurality of markers 76 provided in the target jig is parallel to an imaging plane of the radiation detector 15.

In Step 106, the CPU 52 performs the tomosynthesis imaging described above to create a tomographic image of the target jig. In Step 108, the CPU 52 specifies the three-dimensional coordinate position of the center portion of the plurality of markers 76 provided in the target jig by using the created tomographic image. Note that since the marker 76 according to the present embodiment is a sphere, the diameter gradually increases in the tomographic image, and the three-dimensional coordinate position of the center of each marker 76 can be specified by specifying the position where the diameter is maximum.

In Step 110, the CPU 52 derives the position of the needle tip of the pseudo biopsy needle 90 provided in the target jig as described below, by using the three-dimensional coordinate position of each marker 76 obtained through the above processing.

For example, in a case where the target jig is for vertical puncture as illustrated in FIG. 6 as an example, the radiation image in which the centers of the four markers 76 in the tomographic image obtained by the tomosynthesis imaging are shown is as illustrated in FIG. 14 as an example.

In this case, the radiation images (hereinafter, referred to as "marker images") m1 to m4 of the four markers 76 in the radiation image are reflected as four circles, as illustrated in FIG. 14 as an example.

As described above, in the calibration jig 70A according to the present embodiment, the pseudo biopsy needle 90 and the four markers 76 are positioned such that the position of an intersection of two straight lines in a case of connecting a pair of opposing markers 76 with the straight line matches the position of the needle tip of the pseudo biopsy needle 90. Therefore, as illustrated in FIG. 14 as an example, the CPU 52 derives the three-dimensional coordinate position of an intersection IS of two straight lines of connecting a pair of marker images that are positioned at opposing positions in the marker images m1 to m4, as the position of the needle tip of the pseudo biopsy needle 90. At this time, the CPU 52 corrects the position of each of the marker images m1 to m4 using the read error information. Through the correction, manufacturing errors of each marker 76 can be corrected.

On the other hand, in a case where the target jig is for lateral puncture as illustrated in FIG. 7 as an example, the radiation image in which the centers of the two markers 76 in the tomographic image obtained by the tomosynthesis imaging are shown is as illustrated in FIG. 15 as an example.

In this case, the radiation images of the two markers 76 in the radiation image, that is, the marker images m1 and m2 of the four markers 76 in the radiation image are reflected as two circles, as illustrated in FIG. 15 as an example.

As described above, in the calibration jig 70B according to the present embodiment, the pseudo biopsy needle 90 and the two markers 76 are positioned such that the position of the center of the straight line in a case of connecting a pair of markers 76 with the straight line matches the position of the needle tip of the pseudo biopsy needle 90. Therefore, as illustrated in FIG. 15 as an example, the CPU 52 derives the three-dimensional coordinate position of a center position CE of a straight line of connecting a pair of marker images of the marker images m1 and m2, as the position of the needle tip of the pseudo biopsy needle 90. At this time, the CPU 52 corrects the position of each of the marker images m1 and m2 using the read error information. Similar to the vertical puncture calibration jig 70A, through the correction, manufacturing errors of each marker 76 can be corrected.

In Step 112, the CPU 52 acquires the positional information, which is held by the biopsy unit 26 at this time point and indicates the three-dimensional coordinate position of the needle tip of the pseudo biopsy needle 90 provided in the target jig, by receiving the positional information from the needle position controller 35 of the biopsy unit 26.

In Step 114, the CPU 52 calculates the difference between the corresponding coordinate axes of the derived three-dimensional coordinate position of the needle tip of the pseudo biopsy needle 90 of the target jig in the mammography apparatus 2 and the acquired three-dimensional coordinate position of the needle tip of the pseudo biopsy needle 90 of the target jig in the biopsy unit 26. Accordingly, calibration information for the target jig can be derived.

In Step 116, the CPU 52 stores (registers) the derived calibration information as the calibration information corresponding to the target jig, in the calibration information database 56C, and then ends the present calibration processing.

Thereafter, in the mammography apparatus 2, in a case of actually collecting a specimen by attaching the biopsy needle unit 22 provided with the biopsy needle 21 instead of the calibration jig 70 attached to the biopsy unit 26, the three-dimensional coordinate position obtained from the radiation image is converted into a three-dimensional coordinate position in the biopsy unit 26 using the corresponding calibration information in the calibration information database 56C, which is used for controlling the position of the biopsy needle 21 by the needle position controller 35 of the biopsy unit 26.

As described above, with the calibration jig according to the present embodiment, the calibration jig is provided to a biopsy apparatus used in combination with a mammography apparatus, and is for performing calibration to match three-dimensional coordinate systems of the mammography apparatus and the biopsy apparatus, and the calibration jig includes a pseudo biopsy needle that is a pseudo needle of a biopsy needle that is actually used in the biopsy apparatus; and a marker that has a plurality of parts each of which a positional relationship with a needle tip of the pseudo biopsy needle is known. Accordingly, it is possible to perform calibration to match the three-dimensional coordinate systems of the mammography apparatus and the biopsy apparatus with higher accuracy as compared with a case where the marker and the pseudo biopsy needle are separate bodies.

In addition, with the calibration jig according to the present embodiment, the marker is a plurality of markers each having any one of the plurality of parts individually. Accordingly, as a result of being able to arrange the plurality of parts in a distributed manner, the size of the marker can be made smaller than in a case where one marker has the plurality of parts.

In addition, with the calibration jig according to the present embodiment, a position of the needle tip of the pseudo biopsy needle is different from a position of the marker. Accordingly, the position of the needle tip of the pseudo biopsy needle can be detected with higher accuracy as compared with a case where the position of the needle tip of the pseudo biopsy needle matches the position of the marker.

In addition, with the calibration jig according to the present embodiment, the marker has a spherical shape. Accordingly, the position of the marker can be detected with higher accuracy as compared with a case where the marker has a flat plate shape.

In addition, with the calibration jig according to the present embodiment, an opening portion is provided which allows the needle tip of the pseudo biopsy needle to be accessed from an external jig. Accordingly, the access from the external jig can be performed more easily as compared with a case where the opening portion is not provided.

In addition, with the calibration jig according to the present embodiment, the opening portion allows the access from at least two directions. Accordingly, the access from the external jig can be performed more easily as compared with a case where the opening portion allows the access from only one direction.

Furthermore, with the calibration jig according to the present embodiment, a direction of the access is a direction different from an axial direction of a straight line connecting the needle tip of the pseudo biopsy needle and the plurality of parts of the marker. Accordingly, the access from the external jig can be performed more easily as compared with a case where the direction of the access is the same direction as the axial direction of the straight line connecting the needle tip of the pseudo biopsy needle and the plurality of parts of the marker.

On the other hand, with the mammography apparatus according to the present embodiment, three-dimensional position coordinates of the plurality of parts in the marker of the calibration jig are detected, three-dimensional position coordinates of the needle tip of the pseudo biopsy needle are derived using the detected three-dimensional position coordinates of the plurality of parts, and calibration to match the derived three-dimensional position coordinates of the needle tip and the three-dimensional position coordinates of the needle tip of the pseudo biopsy needle of the biopsy apparatus is performed. Accordingly, similarly to the calibration jig, it is possible to perform calibration to match the three-dimensional coordinate systems of the mammography apparatus and the biopsy apparatus with higher accuracy.

In addition, with the mammography apparatus according to the present embodiment, a manufacturing deviation of a positional relationship between the pseudo biopsy needle and the plurality of parts is corrected. Accordingly, the calibration can be performed with higher accuracy as compared with a case where the correction is not performed.

In addition, with the mammography apparatus according to the present embodiment, the marker of the calibration jig is arranged parallel with the radiation detector in a case where the three-dimensional position coordinates of the plurality of parts are detected. Accordingly, as a result of being able to include the radiation image of each marker in a single image in the tomographic image obtained in this case, the three-dimensional position coordinates of the plurality of parts can be detected more efficiently as compared with a case where the marker is not arranged parallel with the radiation detector.

In addition, with the mammography apparatus according to the present embodiment, the calibration jig is moved in a three-dimensional space by the biopsy apparatus. Accordingly, the calibration can be performed with higher accuracy as compared with a case where the calibration jig is manually moved.

In addition, with the mammography apparatus according to the present embodiment, the calibration jig is used for both vertical puncture and lateral puncture. Accordingly, it is possible to handle both the vertical puncture and the lateral puncture.

Furthermore, with the mammography apparatus according to the present embodiment, the three-dimensional position coordinates of the plurality of parts are detected using a plurality of radiation images obtained by the radiation detector in a state where irradiation directions of the radiation from the radiation irradiator are different. Accordingly, the three-dimensional position coordinates can be detected with higher accuracy as compared with a case where the three-dimensional position coordinates are detected using only a single radiation image.

Note that, in the embodiment, the case where the CPU 52 provided in the controller 50 of the mammography apparatus 2 is applied as a processor of the technique of the present disclosure has been described, but the present disclosure is not limited thereto. For example, the needle position controller 35 of the biopsy unit 26 may be applied as a processor of the technique of the present disclosure.

In addition, in the embodiment, the case where the calibration processing is executed in a case where the biopsy unit 26 is attached to the mammography apparatus 2 has been described, but the present disclosure is not limited thereto. For example, the calibration processing may be executed in a case where the operator of the mammography apparatus 2 inputs an instruction to execute the calibration processing via the operation panel 29 or the like.

In addition, in the embodiment, the case where the marker having a spherical shape is used as the marker provided in the calibration jig has been described, but the present disclosure is not limited thereto. For example, a marker having a flat plate shape may be used as the marker provided in the calibration jig. FIG. 16 illustrates a schematic configuration diagram illustrating an example of a calibration jig 70E for vertical puncture according to this form.

As an example, as illustrated in FIG. 16, the calibration jig 70E includes the substantially rectangular parallelepiped jig main body 71, and the marker 76 having a flat plate shape is provided on the bottom surface of the jig main body 71. The marker 76 according to this form does not transmit radiation.

The mounting hole 78 to which the pseudo biopsy needle 90 is attached is provided at the central portion of the jig main body 71 in plan view. As illustrated in FIG. 16, the pseudo biopsy needle 90 according to this form also has the cylindrical shape of which one end portion is conical, and is fixed to the jig main body 71 in a state where the other end portion side is inserted into the mounting hole 78.

In addition, as illustrated in FIG. 16, the jig main body 71 is provided with the opening portion 82 having a U-shape in cross section from the bottom surface to the front surface of the jig main body 71 such that the distal end portion of the pseudo biopsy needle 90 attached to the mounting hole 78 is exposed. Therefore, the coordinate recognition jig described above can access the needle tip of the pseudo biopsy needle 90 via the opening portion 82.

On the other hand, as illustrated in FIG. 16, the marker 76 according to this form has a rectangular shape of which a corner positioned at the outer peripheral portion of the opening portion 82 is cut out in a shape along the outer peripheral portion in plan view, and is provided such that an intersection of extension lines of a side 76X and a side 76Y that correspond to the cut-out sides matches the position of the needle tip of the pseudo biopsy needle 90. Accordingly, the side 76X and the side 76Y correspond to the plurality of parts described above.

In addition, in the calibration jig 70E, since the marker 76 is not present in the direction of the access, the coordinate recognition jig can access the needle tip of the pseudo biopsy needle 90 without any obstacles.

In addition, as the calibration jig 70, the marker 76 may have a relatively large spherical shape (for example, a spherical shape having a diameter of 5 mm or more) and be single, and the plurality of parts may be two points facing each other on the outer peripheral surface of the single marker 76. In short, as long as a plurality of parts in the technique of the present disclosure can be formed, either a single marker or a plurality of markers can be applied as the marker of the present disclosure.

In addition, in the above embodiment, the case has been described in which the three-dimensional position coordinates of the plurality of parts are detected at a single position, and the three-dimensional position coordinates of the needle tip of the pseudo biopsy needle 90 is derived using the three-dimensional position coordinates of the plurality of parts detected at the single position, but the present disclosure is not limited thereto.

For example, a form may be adopted in which, by moving the calibration jig in the three-dimensional space, the three-dimensional position coordinates of the plurality of parts are detected at a plurality of positions, and the three-dimensional position coordinates of the needle tip at the plurality of positions are derived using the detected three-dimensional position coordinates of the plurality of parts. In addition, in this form, the calibration described above may be performed using the three-dimensional position coordinates of the needle tip of the pseudo biopsy needle at the plurality of derived positions. According to this form, since a plurality of pieces of calibration information are obtained, it is possible to perform calibration with higher accuracy by applying the average value, the median, and the like of the plurality of pieces of calibration information as the calibration information.

In addition, in the above embodiment, the case has been described in which the calibration jig 70 is provided with paired markers 76, that is, the plurality of parts described above, at point-symmetric positions with the needle tip of the pseudo biopsy needle 90 as the center, but the present disclosure is not limited thereto.

The paired markers 76 do not necessarily need to be provided at point-symmetric positions with the needle tip of the pseudo biopsy needle 90 as the center, and any position can be used as the arrangement positions of the markers 76 as long as the positional relationship of the position relative to the position of the needle tip of the pseudo biopsy needle 90 is known. With this configuration, in a case where the position of the marker 76 can be detected, the position of the needle tip of the pseudo biopsy needle 90 can also be specified from the position.

Note that, in the above embodiment, for example, the following various processors can be used as the hardware structure of processing units executing various kinds of processing such as the detection unit 52A, the derivation unit 52B, the calibration unit 52C, and the correction unit 52D. The various processors include, for example, a programmable logic device (PLD) that is a processor of which the circuit configuration can be changed after manufacture, such as a field-programmable gate array (FPGA), and a dedicated electric circuit that is a processor having a dedicated circuit configuration designed to execute a specific process, such as an application specific integrated circuit (ASIC), in addition to the CPU that is a general-purpose processor which executes software (programs) to function as various processing units as described above.

One processing unit may be configured by one of the various processors or a combination of the same or different kinds of two or more processors (for example, a combination of a plurality of FPGAs or a combination of a CPU and an FPGA). In addition, a plurality of processing units may be configured by one processor.

As an example where a plurality of processing units are configured by one processor, first, there is a form where one processor is configured by a combination of one or more CPUs and software as typified by a computer, such as a client and a server, and this processor functions as a plurality of processing units. Second, there is a form where a processor fulfilling the functions of the entire system including a plurality of processing units by one integrated circuit (IC) chip as typified by a system on chip (SoC) or the like is used. In this manner, various processing units are configured by using one or more of the above-described various processors as hardware structures.

Furthermore, specifically, an electric circuit (circuitry) obtained by combining circuit elements, such as semiconductor elements, can be used as the hardware structure of the various processors.

In addition, in the above embodiment, the case has been described in which the calibration processing program 56A is stored (installed) in the storage unit 56 of the mammography apparatus 2 in advance, but the present disclosure is not limited thereto. The calibration processing program 56A may be provided by being recorded in a recording medium, such as a compact disc read only memory (CD-ROM), a digital versatile disc read only memory (DVD-ROM), or a universal serial bus (USB) memory. In addition, the calibration processing program 56A may be downloaded from an external device through a network.

From the above description, the invention described in Additional Remarks described below can be ascertained.

Additional Remark 1

A calibration jig that is attached to a biopsy apparatus used in combination with a mammography apparatus, and that is for performing calibration to match three-dimensional coordinate systems of the mammography apparatus and the biopsy apparatus, the calibration jig comprising:

a pseudo biopsy needle that is a pseudo needle of a biopsy needle that is actually used in the biopsy apparatus; and a marker that has a plurality of parts each of which a positional relationship with a needle tip of the pseudo biopsy needle is known.

Additional Remark 2

The calibration jig described in Additional Remark 1, wherein the marker is a plurality of markers each having any one of the plurality of parts individually.

Additional Remark 3

The calibration jig described in Additional Remark 1 or 2, wherein a position of the needle tip of the pseudo biopsy needle is different from a position of the marker.

Additional Remark 4

The calibration jig described in any one of Additional Remarks 1 to 3, wherein the marker has a spherical shape or a flat plate shape.

Additional Remark 5

The calibration jig described in any one of Additional Remarks 1 to 4, further comprising:

an opening portion which allows the needle tip of the pseudo biopsy needle to be accessed from an external jig.

Additional Remark 6

The calibration jig described in Additional Remark 5, wherein the opening portion allows the access from at least two directions.

Additional Remark 7

The calibration jig described in Additional Remark 6, wherein a direction of the access is a direction different from an axial direction of a straight line connecting the needle tip of the pseudo biopsy needle and the plurality of parts of the marker.

Additional Remark 8

The calibration jig described in any one of Additional Remarks 1 to 7, wherein the plurality of parts are positioned on a surface parallel to a radiation detection surface of the mammography apparatus.

Additional Remark 9

A mammography apparatus provided with a biopsy apparatus having the calibration jig described in any one of Additional Remarks 1 to 8, a radiation irradiator, and a radiation detector that captures a radiation image using radiation emitted from the radiation irradiator, the mammography apparatus comprising:

at least one processor, wherein the processor detects three-dimensional position coordinates of the plurality of parts in the marker of the calibration jig, derives three-dimensional position coordinates of the needle tip of the pseudo biopsy needle using the detected three-dimensional position coordinates of the plurality of parts, and performs calibration to match the derived three-dimensional position coordinates of the needle tip and the three-dimensional position coordinates of the needle tip of the pseudo biopsy needle of the biopsy apparatus.

Additional Remark 10

The mammography apparatus described in Additional Remark 9, wherein the processor corrects a manufacturing deviation of a positional relationship between the pseudo biopsy needle and the plurality of parts.

Additional Remark 11

The mammography apparatus described in Additional Remark 9 or 10, wherein the processor arranges the marker of the calibration jig in parallel with the radiation detector in a case of detecting the three-dimensional position coordinates of the plurality of parts.

Additional Remark 12

The mammography apparatus described in any one of Additional Remarks 9 to 11, wherein the calibration jig is moved in a three-dimensional space by the biopsy apparatus.

Additional Remark 13

The mammography apparatus described in any one of Additional Remarks 9 to 12, wherein the calibration jig is for at least one of vertical puncture or lateral puncture.

Additional Remark 14

The mammography apparatus described in any one of Additional Remarks 9 to 13, wherein the processor detects the three-dimensional position coordinates of the plurality of parts using a plurality of radiation images obtained by the radiation detector in a state where irradiation directions of the radiation from the radiation irradiator are different.

Additional Remark 15

The mammography apparatus described in Additional Remark 14, wherein the processor detects the three-dimensional position coordinates of the plurality of parts at a plurality of positions by moving the calibration jig in a three-dimensional space, and derives the three-dimensional position coordinates of the needle tip at the plurality of positions using the detected three-dimensional position coordinates of the plurality of parts.

Additional Remark 16

The mammography apparatus described in Additional Remark 15, wherein the processor performs the calibration using the derived three-dimensional position coordinates of the needle tip at the plurality of positions.

Additional Remark 17

A program executed in a mammography apparatus provided with a biopsy apparatus having the calibration jig described in any one of Additional Remarks 1 to 8, a radiation irradiator, and a radiation detector that captures a radiation image using radiation emitted from the radiation irradiator, the program causing a computer to execute:

detecting three-dimensional position coordinates of the plurality of parts in the marker of the calibration jig, deriving three-dimensional position coordinates of the needle tip of the pseudo biopsy needle using the detected three-dimensional position coordinates of the plurality of parts, and performing calibration to match the derived three-dimensional position coordinates of the needle tip and the three-dimensional position coordinates of the needle tip of the pseudo biopsy needle of the biopsy apparatus.

What is claimed is:

1. A calibration jig that is attached to a biopsy apparatus used in combination with a mammography apparatus, and that is for performing calibration to match three-dimensional coordinate systems of the mammography apparatus and the biopsy apparatus, the calibration jig comprising:

a pseudo biopsy needle that is a pseudo needle of a biopsy needle that is actually used in the biopsy apparatus; and a marker that has a plurality of parts each of which a positional relationship with a needle tip of the pseudo biopsy needle is known.

2. The calibration jig according to claim 1, wherein the marker is a plurality of markers each having any one of the plurality of parts individually.

3. The calibration jig according to claim 1, wherein a position of the needle tip of the pseudo biopsy needle is different from a position of the marker.

4. The calibration jig according to claim 1, wherein the marker has a spherical shape or a flat plate shape.

5. The calibration jig according to claim 1, further comprising:

an opening portion which allows the needle tip of the pseudo biopsy needle to be accessed from an external jig.

6. The calibration jig according to claim 5, wherein the opening portion allows the access from at least two directions.

7. The calibration jig according to claim 6, wherein a direction of the access is a direction different from an axial direction of a straight line connecting the needle tip of the pseudo biopsy needle and the plurality of parts of the marker.

8. The calibration jig according to claim 1, wherein the plurality of parts are positioned on a surface parallel to a radiation detection surface of the mammography apparatus.

9. A mammography apparatus provided with a biopsy apparatus having the calibration jig according to claim 1, a radiation irradiator, and a radiation detector that captures a radiation image using radiation emitted from the radiation irradiator, the mammography apparatus comprising:

at least one processor, wherein the processor detects three-dimensional position coordinates of the plurality of parts in the marker of the calibration jig, derives three-dimensional position coordinates of the needle tip of the pseudo biopsy needle using the detected three-dimensional position coordinates of the plurality of parts, and performs calibration to match the derived three-dimensional position coordinates of the needle tip and the three-dimensional position coordinates of the needle tip of the pseudo biopsy needle of the biopsy apparatus.

10. The mammography apparatus according to claim 9, wherein the processor corrects a manufacturing deviation of a positional relationship between the pseudo biopsy needle and the plurality of parts.

11. The mammography apparatus according to claim 9, wherein the processor arranges the marker of the calibration jig in parallel with the radiation detector in a case of detecting the three-dimensional position coordinates of the plurality of parts.

12. The mammography apparatus according to claim 9, wherein the calibration jig is moved in a three-dimensional space by the biopsy apparatus.

13. The mammography apparatus according to claim 9, wherein the calibration jig is for at least one of vertical puncture or lateral puncture.

14. The mammography apparatus according to claim 9, wherein the processor detects the three-dimensional position coordinates of the plurality of parts using a plurality of radiation images obtained by the radiation detector in a state where irradiation directions of the radiation from the radiation irradiator are different.

15. The mammography apparatus according to claim 14, wherein the processor detects the three-dimensional position coordinates of the plurality of parts at a plurality of positions by moving the calibration jig in a three-dimensional space, and derives the three-dimensional position coordinates of the needle tip at the plurality of positions using the detected three-dimensional position coordinates of the plurality of parts.

16. The mammography apparatus according to claim 15, wherein the processor performs the calibration using the derived three-dimensional position coordinates of the needle tip at the plurality of positions.

17. A non-transitory storage medium storing a program executed in a mammography apparatus provided with a biopsy apparatus having the calibration jig according to claim 1, a radiation irradiator, and a radiation detector that captures a radiation image using radiation emitted from the radiation irradiator, the program causing a computer to execute:

detecting three-dimensional position coordinates of the plurality of parts in the marker of the calibration jig, deriving three-dimensional position coordinates of the needle tip of the pseudo biopsy needle using the detected three-dimensional position coordinates of the plurality of parts, and performing calibration to match the derived three-dimensional position coordinates of the needle tip and the three-dimensional position coordinates of the needle tip of the pseudo biopsy needle of the biopsy apparatus.

* * * * *